United States Patent [19]

Okada et al.

[11] Patent Number: 4,842,775
[45] Date of Patent: Jun. 27, 1989

[54] REDUCTION OF CARBOXYLIC ESTERS

[75] Inventors: Taiiti Okada, Kyoto; Yasuaki Abe, Takarazuka, both of Japan

[73] Assignee: Takeda Chemical Industries, Ltd., Osaka, Japan

[21] Appl. No.: 186,297

[22] Filed: Apr. 26, 1988

[30] Foreign Application Priority Data

Apr. 27, 1987 [JP] Japan ................................ 62-105795
Apr. 29, 1987 [JP] Japan ................................ 62-105744

[51] Int. Cl.$^4$ ............................................. C07C 50/28
[52] U.S. Cl. ............................... 260/396 R; 568/648; 568/885
[58] Field of Search ................... 260/396 R; 568/648, 568/885

[56] References Cited

U.S. PATENT DOCUMENTS 4,495,104  1/1985  Imada et al. ........................ 568/319
4,559,174 12/1985  Okutani et al. ..................... 568/319

OTHER PUBLICATIONS

Brown et al., J.A.C.S., vol. 78, pp. 2582–88 (1956).
Fieser et al., Reagents for Organic Synthesis, vol. 2, pp. 347–8.
Fieser et al., Reagents for Organic Synthesis, vol. 1, pp. 940–2.
Fieser et al., Reagents for Organic Synthesis, vol. 1, pp. 1053–4.

Primary Examiner—James H. Reamer
Attorney, Agent, or Firm—Wenderoth, Lind & Ponack

[57] ABSTRACT

A method for producing a compound of the formula:

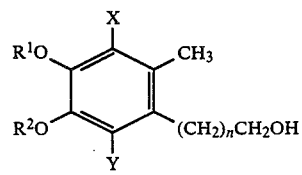

[wherein $R^1$ and $R^2$ each stand for a lower alkyl group; n denotes an integer of 0 to 21; X stands for hydrogen atom or an optionally protected hydroxyl group; and Y stands for an optionally protected hydroxyl group], which comprises reducing an ester compound of the formula:

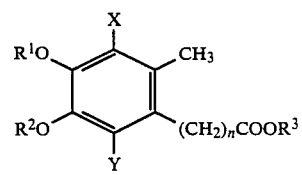

[wherein $R^1$, $R^2$, n, X and Y are of the same meaning as defined above, and $R^3$ stands for a lower alkyl group] with a mixture of sodium borohydride and aluminum chloride. This method gives the desired compound in a high yield, and is advantageous from the industrial point of view.

6 Claims, No Drawings

REDUCTION OF CARBOXYLIC ESTERS

This invention relates to a method for producing 10-(2-hydroxy-3,4-dimethoxy-6-methylphenyl)decan-1-ol and its analogous compounds, which are useful as intermediates for the synthesis of medicines.

6-(10-Hydroxydecyl)-2,3-dimethoxy-5-methyl-1,4-benzoquinone(idebenone) has been known as a compound having specific pharmacological activities such as, among others, immunopotentiating activity, smooth muscle relaxant action, enzyme-activation action in impaired tissues, especially in heart muscle and cerebral tissue. And, as a method of producing idebenone with industrial advantage, the following method (Toku-Kai-Sho 59-39855) has been known: namely, (Step 1)-alkyl 9-(2-hydroxy-3,4-dimethoxy-6-methylbenzoyl)nonanoate is subjected to reduction to give alkyl 10-(2-hydroxy-3,4-dimethoxy-6-methylphenyl)decanoate, (Step 2)-this compound is subjected to further reduction with sodium bis(2-methoxyethoxy)aluminum hydride(Vitride) to give 10-(2-hydroxy-3,4-dimethoxy-6-methylphenyl)decan-1-ol, and (Step 3)-this compound is subjected to oxidation to afford idebenone.

Sodium bis(2-methoxyethoxy)aluminum hydride employed in the above Step 2 has some problems in respect of its safety, because this compound readily reacts with the moisture in air to generate hydrogen causing ignition, and, besides, this compound is a specific reagent and has a difficult point in its stable supply. In consideration of these points, the present inventors have conducted various investigations and found that, by using a mixture of sodium borohydride and aluminum chloride as the reducing agent, 10-(2-hydroxy-3,4-dimethoxy-6-methylphenyl)decan-1-ol and its analogous compounds can be obtained in a good yield with industrial advantage.

The present invention relates to a method of producing a compound of the formula:

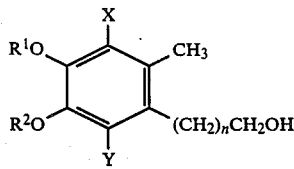

(II)

[wherein $R^1$ and $R^2$ each stand for a lower alkyl group; n denotes an integer of 0 to 21; X stands for hydrogen atom or an optionally protected hydroxyl group; and Y stands for an optionally protected hydroxyl group], which comprises reducing an ester compound of the formula:

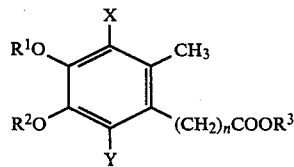

(I)

[wherein $R^1$, $R^2$, n, X and Y are of the same meaning as defined above, and $R^3$ stands for a lower alkyl group] with a mixture of sodium borohydride and aluminum chloride.

Examples of the lower alkyl group shown by $R^1$, $R^2$ and $R^3$ in the above formulas [I] and [II] include those having 1 to 4 carbon atoms such as methyl, ethyl, propyl, etc., and examples of the optionally protected hydroxyl group shown by X and Y include other than free hydroxyl group, for example, a lower alkoxy group having 1 to 3 carbon atoms (e.g. methoxy, ethoxy, etc.), a lower aliphatic carboxylic acyloxy group having 2 to 4 carbon atoms (e.g. acetoxy, propionyloxy, etc.), silyloxy group having 3 to 6 carbon atoms (trimethylsilyloxy, etc.), methoxymethyloxy, etc. The n denotes an integer of 0 to 21, and preferably 8 to 12.

The reduction reaction of the present invention is advantageously conducted in a proper solvent. As the solvent, any one which is capable of dissolving the starting compound [I] and does not hamper the reduction reaction can be employed. Practical examples of such solvent include ethers such as diethyl ether, tetrahydrofuran, dioxane, etc., and aromatic hydrocarbons such as benzene, toluene, xylene, etc. The reaction temperatures usually range from 0° C. to 140° C., preferably 10° C. to 40° C. The amount of sodium borohydride is usually, relative to the starting compound [I], not less than 1.5 times as many moles, such as 1.5 to 10 times as many moles, preferably about 2 to 6 times as many moles. Aluminum chloride is preferably employed in such an amount that the molar ratio of aluminum chloride to sodium borohydride is about 1:3.

This reaction will bring about a more preferable result by allowing a little volume of water to be present in the reaction system. More concretely, the presence of water serves to suppress the formation of an undesired side product, i.e., a compound of the formula [II] wherein one or both of $R^1$ and $R^2$ are hydrogen, thus the yield of the desired compound [II] being further improved. The volume of water to be used ranges usually from 0.1 to 1.7 times as many moles, preferably 0.2 to 1.5 times as many moles relative to the aluminum chloride. When an excess amount of water is used, the desired compound cannot be obtained in a high yield and the reaction time becomes long.

The object compound [II] of the present invention can be led to a compound of the formula:

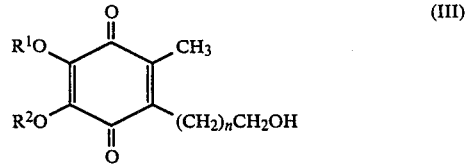

(III)

[wherein each symbol is of the same meaning as defined above], without giving an influence upon the alcoholic hydroxy group, by using an oxidizing agent capable of converting phenol into quinone, for example silver oxide, ferric chloride, manganese dioxide, nitrosodisulfonate, etc. Among them, nitrosodisulfonic acid dialkali metal salt obtained by subjecting an aqueous solution of hydroxylaminedisulfonic acid dialkali metal salt to electrolytic oxidation is preferable.

The following is an explanation of the oxidation reaction of the compound [II] by using, as an oxidizing agent, nitrosodisulfonic acid dialkali metal salt obtained by subjecting an aqueous solution of hydroxylaminedisulfonic acid dialkali metal salt to electrolytic oxidation.

The dialkali metal salt of hydroxylaminedisulfonic acid is exemplified by disodium salt of hydroxylaminedisulfonic acid and dipotassium salt of hydroxylaminedisulfonic acid. The dialkali metal salt of nitrosodisulfonic acid is exemplified by disodium salt of nitrosodisulfonic acid and dipotassium salt of nitrosodisulfonic acid, and the disodium salt of nitrosodisulfonic acid is preferable.

The oxidation of the compound [II] is conducted by dissolving the compound [II] in a water-miscible solvent such as methanol, ethanol, dioxane, tetrahydrofuran, etc., then adding thereto a dialkali metal salt of nitrosodisulfonic acid. The amount of the dialkali metal salt of nitrosodisulfonic acid employed in the method of the present invention is, stoichiometrically, 2.0 times by mol. relative to the compound [II], but, in taking the stability of dialkali metal salt of nitrosodisulfonic acid into consideration, it is usually 2.6 times by mol. or more, preferably 3.0 times by mol. or more. The reaction temperature ranges from 20° C. to 70° C., preferably about 50° C. When the temperature is too low, the reaction proceeds slowly, and, when the temperature is high, decomposition of the dialkali metal salt of nitrosodisulfonic acid is promoted and undesirable side-reactions are apt to occur, thus being not preferable. The reaction time varies with the concentration of the starting compound [II], the solvent employed, the amount of the dialkali metal salt of nitrosodisulfonic acid, the reaction temperature, etc., but, usually, when the starting compound is completely consumed, the reaction is terminated. For example, by means of thin-layer chromatography, high performance liquid chromatography, gas chromatography, etc., decrease of the starting material is traced with the passage of time, and when the starting material is not detected any more, the reaction is terminated. In the case of conducting the reaction at 50° C., the reaction usually is complete within two hours. The aqueous solution of the dialkali metal salt of nitrosodisulfonic acid employed as an oxidizing agent can be obtained by subjecting an aqueous solution of a dialkali metal salt of hydroxylaminedisulfonic acid to electrolytic oxidation which is conducted in a conventional electrochemical cell. This electrochemical cell is optionally equipped with a separator or diaphragm. In general, use of a filter-press type electrochemical cell equipped with cation-exchange membrane is preferable. The heat generating from the reaction can be suppressed by controlling the rise of cell voltage by having a narrow electrode gap and, besides, by cooling outside both anolyte and catholyte circulated through both chambers with a high speed. The anode and the cathode are prepared from any material commonly used as electrodes in the field of electrochemistry, for example, carbon, platinum, stainless steel, palladium, nickel, nickel alloy, etc. In general, use of stainless steel mesh electrode is preferable. The electrolytic cell can be equipped with a stirring device, and it is also possible to circulate the reaction mixture by the use of a pump.

The electrolytic oxidation can be conducted by applying a voltage of 0.5 to 50 volts to an aqueous solution containing dialkali metal salt of hydroxylaminedisulfonic acid. In general, the reaction is preferably conducted by using 2 to 20 volts. The electric current passing through the solution is of a current density up to 50 ampere per square decimeter. In general, it is preferable to use a current density of 2 to 20 ampere per square decimeter. For carrying out the electrolytic oxidation more effectively, it is possible to add a conventional electrolyte to the aqueous solution. Examples of such an electrolyte include sodium hydroxide, sodium acetate, sodium carbonate, sodium hydrogen carbonate, sodium phosphate, sodium chloride, etc. In general, the amount of an electrolyte to be added is preferably in the range of from 0.1 to 30 weight % relative to the aqueous solution. The aqueous solution to be subjected to electrolytic oxidation contains, in general, dialkali metal salt of hydroxylaminedisulfonic acid at a concentration of at least 0.1 mol., preferably 0.1 mol. to 2 mol., relative to one liter of the solution. The electrolytic oxidation can be carried out at a temperature ranging from $-15°$ C. to 50° C. In general, this reaction is preferably conducted at a temperature ranging from 0° C. to 35° C. The electrolytic oxidation can be carried out for at least 0.5 hour or a longer period of time. In general, it is preferable to conduct the oxidation for one to 10 hours.

At the time of starting the electrolytic oxidation, the pH of the aqueous solution of dialkali metal salt of hydroxylaminedisulfonic acid is adjusted at 10 to 13, preferably around 11.5, to thereby maximize the yield of dialkali metal salt of nitrosodisulfonic acid.

The compound [III] has an immuno-potentiating activity, smooth muscle relaxant action, an enzyme-activation action in brain tissue, etc.

The starting compound [I] in the present invention can be obtained by subjecting a compound represented by the general formula:

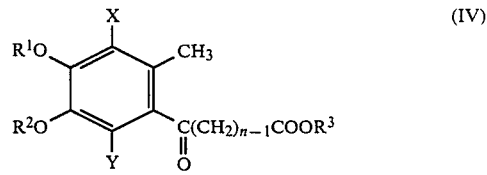

(IV)

[wherein each symbol is of the same meaning as defined above] to reduction by a conventional method, for example, Clemensen reduction using zinc amalgam and hydrochloric acid, Wolff-Kishner reduction of hydrazone, desulfurative reduction of dithioacetal or catalytic reduction.

In the present invention, by using a mixture of sodium borohydride and aluminum chloride, the compound [I] is subjected to reduction to obtain the compound [II] in a good yield, and, by adding water to the reaction system, the object compound [II] can be produced in a high yield and with a high purity and, besides, with good reproducibility.

By the following examples and reference examples, the present invention will be described in more detail.

REFERENCE EXAMPLE 1

To a solution of methyl 9-(2-hydroxy-3,4-dimethoxy-6-methylbenzoyl)nonanoate (2.0 kg) in ethyl acetate (10 l) were added 5% palladium carbon (water content: 50%) (400 g) and sulfuric acid (10 ml). The mixture was stirred for 5 hours at 30° C. to 40° C. in hydrogen streams (hydrogen pressure: ca. 8.5 kg/cm$^2$ G). The catalyst was filtered off, and the ethyl acetate layer was washed with water (10 l), 5% sodium hydrogen carbonate (10 l) and water (10 l), successively. The ethyl acetate layer was concentrated to obtain 10-(2-hydroxy-3,4-dimethoxy-6-methylphenyl)decanoate (1.8 kg) as an oily product.

Infrared absorption spectrum $\lambda_{max}^{film}$ cm$^{-1}$: 3450 (OH), 1740 (COOCH$_3$).

Nuclear magnetic resonance spectrum $\delta_{ppm}^{CDCl_3}$: 1.10 to 1.87 (14 H, multiplet, —(CH$_2$)$_7$—), 2.17 to 2.57 (4 H, multiplet, ring CH$_2$, CH$_2$CO), 2.27 (3 H, singlet, ring CH$_3$), 3.63 (3 H, singlet, COOCH$_3$), 3.80 (3 H, singlet, OCH$_3$), 3.85 (3 H, singlet, OCH$_3$), 5.80 (1 H, singlet, OH), 6.27 (1 H, singlet, ring H).

EXAMPLE 1

In tetrahydrofuran (1.8 l) was dissolved methyl 10-(2-hydroxy-3,4-dimethoxy-6-methylphenyl)decanoate (881 g, 2.5 mol.). To the solution was added a suspension of sodium borohydride (340 g, 9 mol.) in tetrahydrofuran (10.7 l), and the mixture was stirred. To the resulting suspension was added water (75 ml, 4.16 mol.). Aluminum chloride (400 g, 3 mol.) was dissolved in tetrahydrofuran (6.0 l). The solution was added dropwise to the above-mentioned suspension at a given rate in the course of 90 minutes, during which period the inner temperature of the reaction mixture was kept at 25±2° C. Then, the reaction mixture was stirred at the same temperature for further 30 minutes, which was then cooled to about 15° C. To the reaction mixture was added water (22 l) dropwise to cause decomposition, to which was then added dropwise hydrochloric acid (2.7 l). The mixture was subjected to extraction twice with 9 l each portion of toluene. Then, the toluene layers were combined and washed with a 5% aqueous solution of sodium hydrogen carbonate (4.4 l), followed by further washing with water (4.4 ). The toluene layer was concentrated under reduced pressure to obtain 10-(2-hydroxy-3,4-dimethoxy-6-methylphenyl)decan-1-ol (805 g, 2.48 mol., yield 99.2%) as an oily product.

Infrared absorption spectrum $\nu_{max}^{neat}$ cm$^{-1}$: around 3400 (OH).

Nuclear magnetic resonance spectrum $\delta_{ppm}^{CDCl_3}$: 1.10 to 1.80 (16 H, multiplet, —(CH$_2$)$_8$—), 2.22 (3 H, singlet, CH$_3$), 2.40 to 2.75 (2 H, multiplet, CH$_2$), 8.50 to 8.70 (2 H, multiplet, CH$_2$), 3.80 (3 H, singlet, OCH$_3$), 8.84 (3 H, singlet, OCH$_3$), 6.25 (1 H, singlet, ring H).

EXAMPLE 2

Investigation was conducted on the relationship of the volume of water added with the yield of 10-(2-hydroxy-3,4-dimethoxy-6-methylphenyl)decan-1-ol. In tetrahydrofuran (35.7 ml) was dissolved methyl 10-(2-hydroxy-3,4-dimethoxy-6-methylphenyl)decanoate(-methyl decanoate) (17.3 g, 49.1 mmol.). The solution was added to a suspension of sodium borohydride (6.8 g, 80 mmol.) in tetrahydrofuran (214.5 ml), and the mixture was stirred. A given volume of water was precisely measured (as described in Table 1), which was added to this suspension. In tetrahydrofuran (142 ml) was dissolved aluminum chloride (8.0 g, 60 mmol.). The solution was added dropwise to the above-mentioned suspension at the internal temperature of 25°±2° C. taking 90 to 120 minutes. The reaction mixture was then stirred for 30 minutes while keeping its temperature at 25°±2° C. The reaction mixture was then cooled to 15°±2° C., to which was added dropwise water (446 ml). To the mixture was added dropwise hydrochloric acid (53.5 ml) gradually, during which time the temperature of the reaction mixture was kept at temperatures not exceeding 20° C. The reaction mixture was then subjected to extraction twice with 178.5 ml each portion of toluene. The toluene layers were combined and washed twice with water (89.5 ml). The toluene layer was concentrated under reduced pressure to obtain 10-(2-hydroxy-3,4-dimethoxy-6-methylphenyl)decan-1-ol(decanol compound) as an oily product. Table 1 shows the relationship of the volume of water added with the yield of the decanol compound and with the amount of di-OH compound produced.

TABLE 1

Relationship of the volume of water added with the yield of the decanol and with the amount of di-OH produced

| No. | Volume of water added ml | molar ratio[1] | Yield of decanol compound (%) | Yield of di-OH[2] compound (%) |
|---|---|---|---|---|
| 1 | 0 | 0.0 | 94.2 | 9.2 |
| 2 | 0 | 0.0 | 95.4 | 6.9 |
| 3 | 0.8 | 0.74 | 96.9 | 3.3 |
| 4 | 0.8 | 0.74 | 98.2 | 2.8 |
| 5 | 1.0 | 0.93 | 98.3 | 1.8 |
| 6 | 1.0 | 0.93 | 98.3 | 2.7 |
| 7 | 1.5 | 1.39 | 99.2 | 0.6 |
| 8 | 1.5 | 1.39 | 99.2 | 1.4 |
| 9 | 1.8 | 1.67 | 99.0 | 1.2 |
| 10 | 1.8 | 1.67 | 98.7 | 1.7 |
| 11 | 2.0 | 1.85 | 97.6 | 0.5 |
| 12 | 2.0 | 1.85 | 90.4 | 0.0 |
| 13 | 2.5 | 2.31 | 85.3 | 0.0 |
| 14 | 2.5 | 2.31 | 90.6 | 0.0 |

Note
[1] Molar ratio = $\frac{\text{Number of moles of water added}}{\text{Number of moles of aluminum chloride}}$ Note
[2] Yield of di-OH compound = $\frac{\text{peak area of di-OH compound}}{\text{peak area of decanol compound}} \times 100$ di-OH compound: 10-(2,3-dihydroxy-4-methoxy-6-methylphenyl)decan-1-ol

REFERENCE EXAMPLE 2

Synthesis of an aqueous solution of disodium salt of hydroxylaminedisulfonic acid In water (7.5 l) was dissolved sodium nitrite (1875 g), to which was added dropwise a 35 w/w% aqueous solution of sodium hydrogen sulfite (11.5 l), while maintaining the temperature of the solution at 0° C. or below. To the mixture was then added dropwise acetic acid (2,860 ml) at temperatures not exceeding 5° C., followed by stirring for 90 minutes at 5° C. or below. To the resultant was then added dropwise a 30 w/w% aqueous solution of caustic soda (3,125 ml) at 10° C. or below, followed by dropwise addition of a 25 w/w% aqueous solution of sodium carbonate (20 l) to obtain an aqueous solution of disodium salt of hydroxylaminedisulfonic acid capable of being subjected to immediate electrolytic oxidation. The yield was about 84%.

REFERENCE EXAMPLE 3

Synthesis of an aqueous solution of disodium salt of nitrosodisulfonic acid by electrolytic oxidation Monopolar, two-compartment type and filter press type electrochemical cell (active electrode area: 4.5 dm$^2$/cell×2 cells) was charged with an aqueous solution of disodium salt of hydroxylaminedisulfonic acid (6 to 8 l) as the anolyte and with a 10 w/w% aqueous solution of sodium carbonate (6 to 8 l) as the catholyte, then circulation was conducted by means of a pump. By application of an electric current for 2 to 3 hours under given electrolytic conditions (current density: 8 A/dm$^2$, circulation linear velocity: 10.4 cm/sec., temperature: 15° C.), an aqueous solution of disodium nitrosodisulfonate was obtained in a yield of 90% or higher.

REFERENCE EXAMPLES 4 TO 7

In methanol (5.4 l) was dissolved 10-(2-hydroxy-3,4-dimethoxy-6-methylphenyl)decan-1-ol (271 g), to which was added an aqueous solution of disodium nitrosodisulfonate (6.7 l, content 0.359 mol./l) synthesized by means of electrolytic oxidation. The mixture was stirred for two hours while keeping the temperatures at 50°±2° C. After confirmation of disappearance of the starting material by thin-layer chromatography, water (8.6 l) was added to the reaction mixture, followed by extraction twice with toluene (5.5 and 2.7 l). The toluene layers were combined and washed with water. The toluene layer was concentrated under reduced pressure to obtain a crude product, 6-(10-hydroxydecyl)-2,3-dimethoxy-5-methyl-1,4-benzoquinone (288 g, content 94.8%, yield 96.9%). This crude product (20 g) was recrystallized from a mixture of toluene (60 ml) and n-hexane (180 ml). The crystals were dissolved in toluene (60 ml), and the solution was allowed to pass through a precoated layer of activated alumina (30 g). The filtrate was concentrated under reduced pressure, and the concentrate was recrystallized again from a mixture of toluene (55 ml) and n-hexane (165 ml). The crystals were further recrystallized from 50% ethanol (108 ml), followed by drying to obtain 6-(10-hydroxydecyl)-2,3-dimethoxy-5-methyl-1,4-benzoquinone (16.2 g) as orange-yellow crystals, m.p. 54.0° C.

Infrared absorption spectrum $\nu_{max}^{KBr}$ cm$^{-1}$: 3550 (OH), 1660, 1650, 1610 (1,4-benzoquinone).

Nuclear magnetic resonance spectrum $\delta_{ppm}^{CDCl_3}$: 1.1 to 1.8 (16 H, multiplet,—(CH$_2$)$_8$—), 2.00 (3 H, singlet, CH$_3$), 2.43 (2 H, triplet, J=7 Hz, CH$_2$), 3.63 (2 H, triplet, J=6 Hz, CH$_2$OH), 3.97 (6 H, singlet, OCH$_3$).

Examples using an aqueous solution of disodium nitrosodisulfonate synthesized by means of electrolytic oxidation are described in Table 2.

TABLE 2

Oxidation of 1 by the use of an aqueous solution of disodium nitrosodisulfonate prepared by electrolytic oxidation

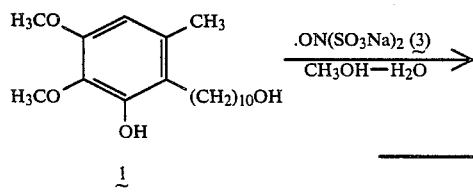

1

TABLE 2-continued

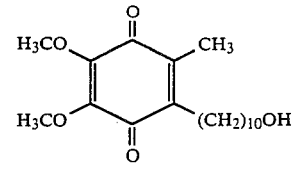

2

| Example No. | Amount Charged | | | Reaction Conditions | | 2 | |
|---|---|---|---|---|---|---|---|
| | 1 (g) | 3 (mol/l) | CH$_3$OH (l) | Temperature (°C.) | Time (hr) | Yield (g) | Yield (%) |
| 4 | 271 | 2.41/6.7 | 5.4 | 48–53 | 2.0 | 273 | 96.9 |
| 5 | 262 | 2.32/6.7 | 5.2 | 48–53 | 2.0 | 266 | 97.3 |
| 6 | 308 | 2.96/7.6 | 6.1 | 48–52 | 2.0 | 318 | 98.9 |
| 7 | 372 | 3.40/7.6 | 7.6 | 48–50 | 2.0 | 380 | 98.0 |

REFERENCE EXAMPLES 8 TO 10

In methanol (110 l) was dissolved 10-(2-hydroxy-3,4-dimethoxy-6-methylphenyl)decan-1-ol (6.84 kg). To this solution were added sodium acetate (27.4 kg) and water (110 l). To the mixture was then added dipotassium nitrosodisulfonate (23.5 kg, content 69.9%), which was stirred at 50°±3° C. for 3 hours. After confirming disappearance of the starting material by means of thin-layer chromatography, water (550 l) was added to the mixture, which was stirred at 10° C. or below for 30 minutes or longer, then precipitating crystals were separated by centrifuge. Wet crystals thus collected were dissolved in ethyl acetate (40 l), followed by washing with water (25). The ethyl acetate layer was concentrated under reduced pressure to obtain a crude product 6-(10-hydroxydecyl)-2,3-dimethoxy-5-methyl-1,4-benzoquinone (6.70 kg, yield 93.9%). Reference examples using dipotassium nitrosodisulfonate (Fremy's salt) are described in Table 3.

TABLE 3

Oxidation of 1 by the use of dipotassium nitrosodisulfonate (crystals)

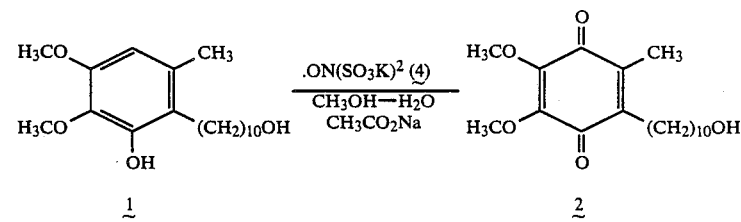

| Reference Example No. | Amount Charged | | | | | Reaction Conditions | | 2 | |
|---|---|---|---|---|---|---|---|---|---|
| | 1 (kg) | 4$^1$ (kg) | CH$_3$CO$_2$Na (kg) | CH$_3$OH (l) | H$_2$O (l) | Temperature (°C.) | Time (hr) | Yield (kg) | Yield (%) |
| 8 | 6.84 | 16.4 | 27.4 | 110 | 110 | 48–52 | 3.0 | 6.70 | 93.9 |
| 9 | 7.57 | 18.2 | 30.3 | 120 | 120 | 48–51 | 3.0 | 7.22 | 91.4 |
| 10 | 10.03 | 24.0 | 40.0 | 160 | 160 | 47–52 | 3.0 | 9.78 | 93.5 |

$^1$Meaning substantial amount charged (= apparent amount charged × content)

We claim:
1. A method for producing a compound of the formula:

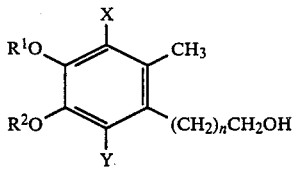
(II)

wherein $R^1$ and $R^2$ each stand for a lower alkyl group; n denotes an integer of 0 to 21; X stands for a hydrogen atom or an optionally protected hydroxyl group; and Y stands for an optionally protected hydroxyl group, which comprises reducing an ester compound of the formula:

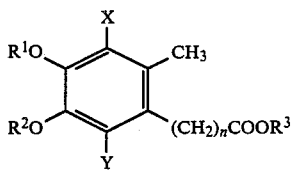
(I)

wherein $R^1$, $R^2$, n, X and Y each has the same meaning as defined above, and $R^3$ stands for a lower alkyl group, with a mixture of sodium borohydride and aluminum chloride in the presence of water.

2. A method as claimed in claim 1, wherein sodium borohydride is used in an amount of not less than 1.5 moles per mole of the ester compound.

3. A method as claimed in claim 1, wherein sodium borohydride is used in an amount of about 3 moles per mole of aluminum chloride.

4. A method as claimed in claim 1, wherein water is used in an amount of 0.1 to 1.7 mole per moles of aluminum chloride.

5. A method as claimed in claim 1, wherein the compound of formula (II) is oxidized by an oxidizing agent to give a compound of the formula:

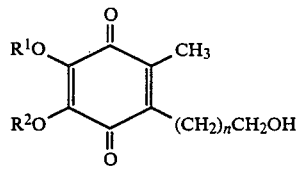

wherein $R^1$ and $R^2$ each stand for a lower alkyl group and n denotes an integer of 0 to 21.

6. A method as claimed in claim 5, wherein the oxidizing agent is nitrosodisulfonic acid dialkali metal salt obtained by subjecting an aqueous solution of hydroxylaminedisulfonic acid dialkali metal salt to electrolytic oxidation.

* * * * *